US011580626B1

(12) United States Patent
Weiss (10) Patent No.: US 11,580,626 B1
(45) Date of Patent: Feb. 14, 2023

(54) COMPUTER APPARATUS AND METHODS FOR GENERATING COLOR COMPOSITE IMAGES FROM MULTI-ECHO CHEMICAL SHIFT-ENCODED MRI

(71) Applicant: Kenneth L. Weiss, Miami, FL (US)

(72) Inventor: Kenneth L. Weiss, Miami, FL (US)

( * ) Notice: Subject to any disclaimer, the term of this patent is extended or adjusted under 35 U.S.C. 154(b) by 42 days.

(21) Appl. No.: 16/795,557

(22) Filed: Feb. 19, 2020

Related U.S. Application Data (60) Provisional application No. 62/807,659, filed on Feb. 19, 2019.

(51) Int. Cl.

| | | |
|---|---|---|
| *G06K 9/00* | (2022.01) | |
| *G06T 5/50* | (2006.01) | |
| *G06T 9/00* | (2006.01) | |
| *G06T 7/00* | (2017.01) | |
| *G16H 30/40* | (2018.01) | |
| *G16H 30/20* | (2018.01) | |
| *G16H 50/70* | (2018.01) | |
| *G16H 50/20* | (2018.01) | |
| *A61B 5/00* | (2006.01) | |
| *A61B 5/055* | (2006.01) | |
| *G06T 7/90* | (2017.01) | |
| *G06F 3/0482* | (2013.01) | |

(52) U.S. Cl.
CPC ................ *G06T 5/50* (2013.01); *A61B 5/055* (2013.01); *A61B 5/4872* (2013.01); *A61B 5/7267* (2013.01); *G06T 7/0012* (2013.01); *G06T 7/90* (2017.01); *G06T 9/00* (2013.01); *G16H 30/20* (2018.01); *G16H 30/40* (2018.01); *G16H 50/20* (2018.01); *G16H 50/70* (2018.01); *A61B 2576/00* (2013.01); *G06F 3/0482* (2013.01); *G06T 2207/10024* (2013.01); *G06T 2207/10088* (2013.01); *G06T 2207/20081* (2013.01); *G06T 2207/20084* (2013.01); *G06T 2210/41* (2013.01)

(58) Field of Classification Search
None
See application file for complete search history.

(56) References Cited

U.S. PATENT DOCUMENTS

| | | | | |
|---|---|---|---|---|
| 2009/0143669 | A1* | 6/2009 | Harms | A61B 5/055 600/410 |
| 2015/0145514 | A1* | 5/2015 | Sharma | G01R 33/243 324/309 |
| 2017/0350951 | A1* | 12/2017 | Samsonov | G01R 33/5605 |
| 2018/0313925 | A1* | 11/2018 | Parker | G01R 33/56341 |

(Continued)

OTHER PUBLICATIONS

Omer ("The Relation between Color Spaces and Compositional Data Analysis Demonstrated with Magnetic Resonance Image Processing Applications", Austrian Journal of Statistics, Sep. 2018, vol. 47, 34-46). (Year: 2018).*

(Continued)

*Primary Examiner* — Wei Wen Yang (57) ABSTRACT

A computer apparatus and methods generate multi-parametric color composite images from multi-echo chemical shift encoded (CSE) MRI. Some embodiments use inherently co-registered images (i.e., image maps) that are combined into a single intuitive composite color image. The color (e.g., brightness, hue, and/or saturation) reflects in part the water and fat content, and other properties, particularly T2* relaxation (related to magnetic susceptibility) of the tissue.

20 Claims, 7 Drawing Sheets

(56) References Cited

U.S. PATENT DOCUMENTS

| | | | |
|---|---|---|---|
| 2020/0123618 A1* | 4/2020 | Batenchuk | G06K 9/4652 |
| 2020/0226422 A1* | 7/2020 | Li | G06N 3/08 |
| 2020/0264253 A1* | 8/2020 | Shin | A61B 5/7264 |
| 2020/0408863 A1* | 12/2020 | Liang | G01R 33/5615 |
| 2021/0055364 A1* | 2/2021 | Madhuranthakam | G01R 33/5602 |

OTHER PUBLICATIONS

Of Kather ("Color-coded visualization of magnetic resonance imaging multiparametric maps" Scientific Reports, 2017, pp. 1-11). (Year: 2017).*

* cited by examiner

COMPUTER APPARATUS AND METHODS FOR GENERATING COLOR COMPOSITE IMAGES FROM MULTI-ECHO CHEMICAL SHIFT-ENCODED MRI

CROSS-REFERENCE TO RELATED APPLICATIONS

This application claims the benefit of U.S. Provisional Application No. 62/807,659, filed Feb. 19, 2019, which is hereby incorporated herein by reference in its entirety.

FIELD

The disclosure of this application relates, in general, to techniques by which images can be created, analyzed and presented to health care professionals or other individuals or systems.

BACKGROUND

Dixon is an MRI technique that uses the difference in resonant frequencies of water and fat to acquire in-phase (IP) and opposed-phase (OP) images and derive water (W) and fat (F) images in conjunction with phase maps. If W>F: W=½(OP+IP) & F=½(IP−OP); if F>W: F=½(OP+IP) & W=½(IP−OP). IP, OP, W, and F values are interdependent. Given any three, the fourth can be derived. Radiologists will often examine and/or compare several of the four images to make a diagnosis. Additional details regarding the Dixon technique can be found in the 1984 article by Dixon, W. T. titled "Simple proton spectroscopic imaging" Radiology 153, 189-194, which is hereby incorporated by reference.

The Dixon technique, often performed in a 3D breath hold acquisition, has increasingly become a mainstay for body imagers and can help identify and characterize focal lesions and assess for steatosis (i.e. fatty change) or excess iron in the liver and other organs. Beyond the abdomen, Dixon sequencing primarily substitutes for other chemical shift based fat suppression techniques (e.g. chemical presaturation and selective excitation) due to Dixon's relative insensitivity to magnetic field inhomogeneity and susceptibility. For this fat suppression case, typically only W images are reviewed, and little attention is paid to the IP, OP, and F images. Consequently, potentially important information contained in the IP, OP, and F images may be overlooked.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

DESCRIPTION OF THE INVENTION

The invention relates to a computer apparatus and methods to generate multi-parametric color composite images from multi-echo chemical shift encoded (CSE) MRI. Some embodiments of the invention use three inherently co-registered images (i.e., image maps) that are combined into a single intuitive composite color image. The color (e.g., brightness, hue, and/or saturation) reflects in part the water and fat content, and other properties, particularly T2* relaxation (related to magnetic susceptibility) of the tissue.

Figure 1A:
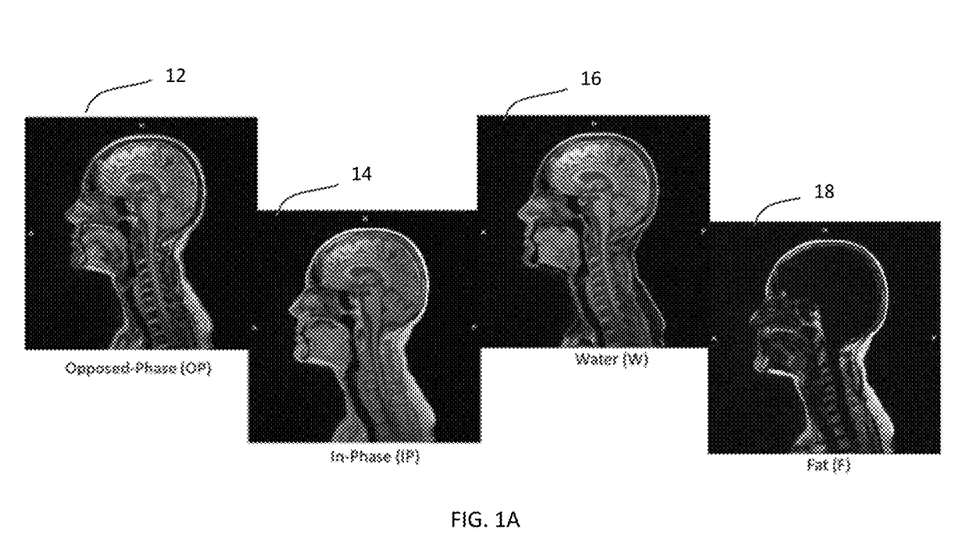
FIG. 1A shows a series of traditional gray-scale MRI images of the head and neck of a person where the OP and IP images were acquired using a Dixon sequence and the W and F were derived from the OP and IP images.

The three or more images used to encode the multi-parametric composite image can be obtained from dual-echo Dixon or longer multi-echo chemical shift-encoded (CSE) MRI, the latter potentially providing confounder corrected proton density fat fraction (PDFF), R2*, and other quantitative image maps in addition to the more qualitative fat (F) and water (W) maps typically derived from a two-point Dixon sequence. In the case of dual-echo Dixon, in-phase (IP), opposed-phase (OP) and water (W) images are typically used to produce the composite image. FIG. 1A shows a series of traditional gray-scale MRI images of the head and neck of a person where the OP (12) and IP (14) images were acquired using a Dixon sequence and the W (16) and F (18) were derived from the OP (12) and IP (14) images.

The color composite facilitates interpretation of these complex information-rich datasets and may reduce the number of requisite images to be stored and reviewed, thereby extending the clinical utility of multi-echo CSE MRI. Examining a single multiparametric color encoded image can reduce examination time and diagnostic errors as compared to the traditional method of side-by-side comparison of grayscale images. This is particularly true of multi-phasic exams and multiplanar reconstructions which can require a truly herculean effort to compare and/or examine all the images produced in a single study. The color-encoded images of the present invention may also extend the utility of Dixon fat suppression studies where IP, OP, and F images are often overlooked while examining W images.

In some embodiments, the encoding produces a composite image with substantial portions that appear as grayscale. Images with grayscale and color are easier for clinicians to review and interpret due to the familiarity with grayscale and the contrast between colored tissue and gray tissue. In some embodiments, image voxels appear as shades of gray for image voxels whose MRI signal derives from water protons without appreciable contribution from lipid protons or T2* decay. Appreciable fat content and/or T2* decay is an amount that provides a discernable amount of color in the composite image to a person viewing the image when fat content and/or T2* relaxation are configured to contribute to the hue and saturation.

In one embodiment of the invention, the image maps used to create the color composite may be generated using the Dixon technique and selected from IP, OP, W, and F. The image maps can be assigned a color in the RGB color space. Tissues containing only W signal (e.g. normal brain, spinal cord, intervertebral discs and liver) typically demonstrate similar OP, IP, and W signal intensities on Dixon imaging. In RGB color space, simple assignment of the OP, IP and W maps to the red (R), green (G) and blue (B) color channels yield six different possible orderings (3×2×1). In any of these cases, where the voxels have similar values for OP, IP, and W, the voxels will appear as gray. Where the values for OP, IP, and W are appreciably different, the voxels have a color that deviates from gray.

Figure 1B:
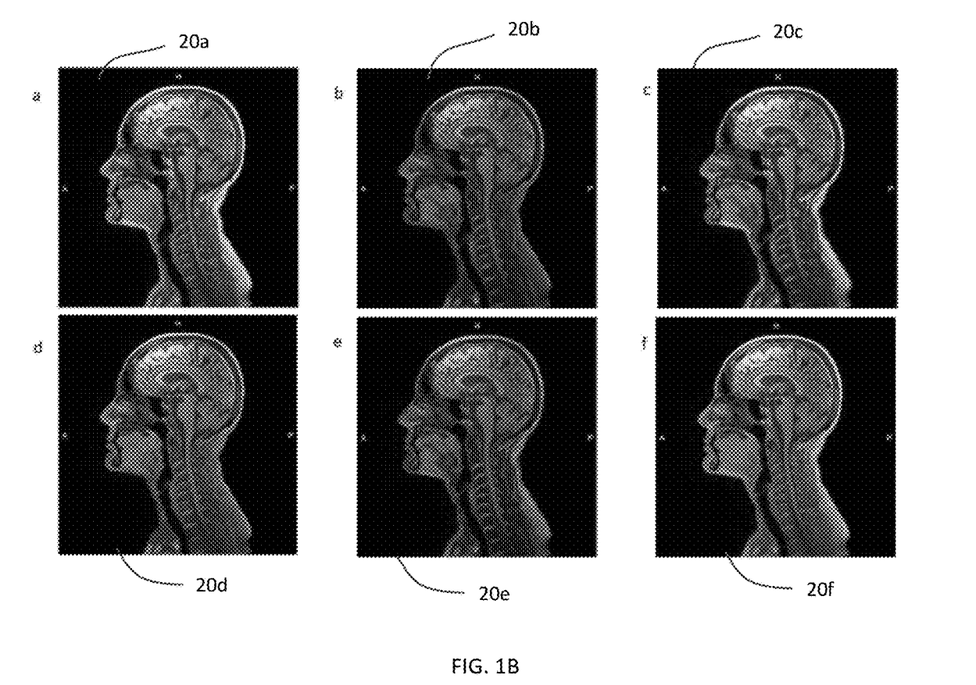
FIG. 1B shows six color encoded RGB composite images of IP, OP, and W.

For FIG. 1B, a Matlab program was created to generate color DICOM composite images and applied to representative Dixon datasets to produce color schemes. FIG. 1B shows the images 20a-20f with the six different color schemes that result from simple direct assignments of any of OP (12), IP (14), and W (16) (from FIG. 1A) to the R, G, and B color channels. The color scheme of image 20c is of particular interest because it produces yellow voxels where fat content is high. Image 20c was produced using IP=R, OP=G, and W=B. Fat content shows yellow, water plus fat shows red, and magnetic susceptibility/increased T2* relaxation shows green. A color scheme where fat appears yellow and fat plus water appears red is particularly intuitive because biologic fat typically has a yellowish hue, fatty marrow is commonly termed yellow marrow and hematopoietic marrow containing both water and fat protons is commonly termed red marrow.

Figure 2A:
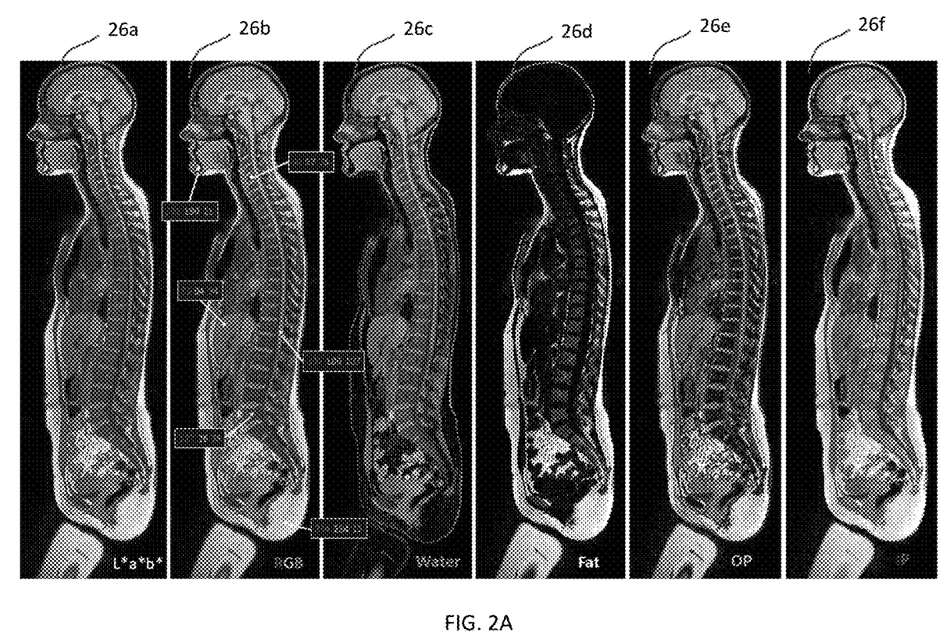
FIG. 2A shows color composite images in the RGB and CIE L*a*b* color spaces, the W, OP, and IP images used to generate these composite images, and the F map typically created but not used in the generation of these composites.
Figure 2B:
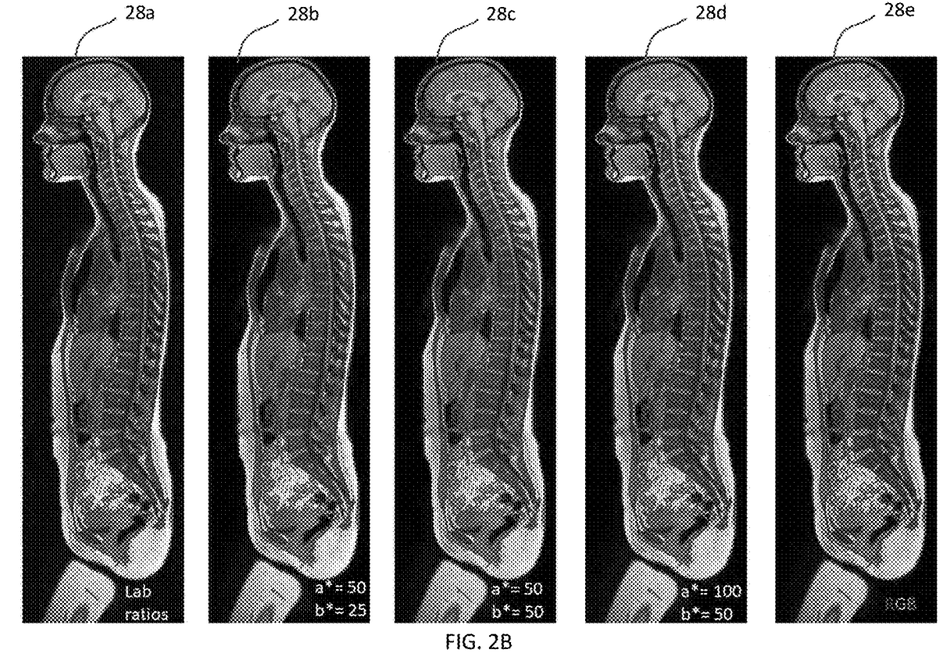
FIG. 2B shows CIE L*a*b* encoding of W, OP, and IP images utilizing different CIE L*a*b ratios and values.

The color composite may be encoded in one or more of several different color spaces. Examples of major color models include the following or variants thereof: RGB, CIE, YUV, HSL/HSV, and CMYK. FIG. 2A shows color composite images 26a and 26b in the RGB and CIE L*a*b* color spaces. In addition, FIG. 2A includes the W image 26c, OP image 26e, and IP image 26f that were used to generate the RGB composite image 20a and L*a*b* composite image 20b. In FIG. 2A, novel multiparametric color encoding programs were created in Matlab to combine OP (26e), IP (26f), and W (26c) series so that tissues containing only W signal (e.g. brain, cord, discs) appear grayscale, F appears yellow (red+green), tissues or "Indian ink artifact" containing both W and F appear red-magenta, and tissues exhibiting significant T2*decay appear cyan-green. To achieve this in RGB color space; IP (36), OP (34), and W (30) series were respectively assigned to the red (R), green (G), and blue (B) channels. (FIG. 2A) To achieve this in CIE L*a*b* color space, designed to more closely parallel human perception, we set: L=IP+OP, a=(IP−OP)/(IP+OP), and b=(IP+OP−2W)/(IP+OP) or L=x*(IP+OP), a=y*(IP−OP) and b=z*(IP+OP−2W), with RGB appearance approximated with x, y, z values of 50, 100, and 50 respectively.

Figure 8:
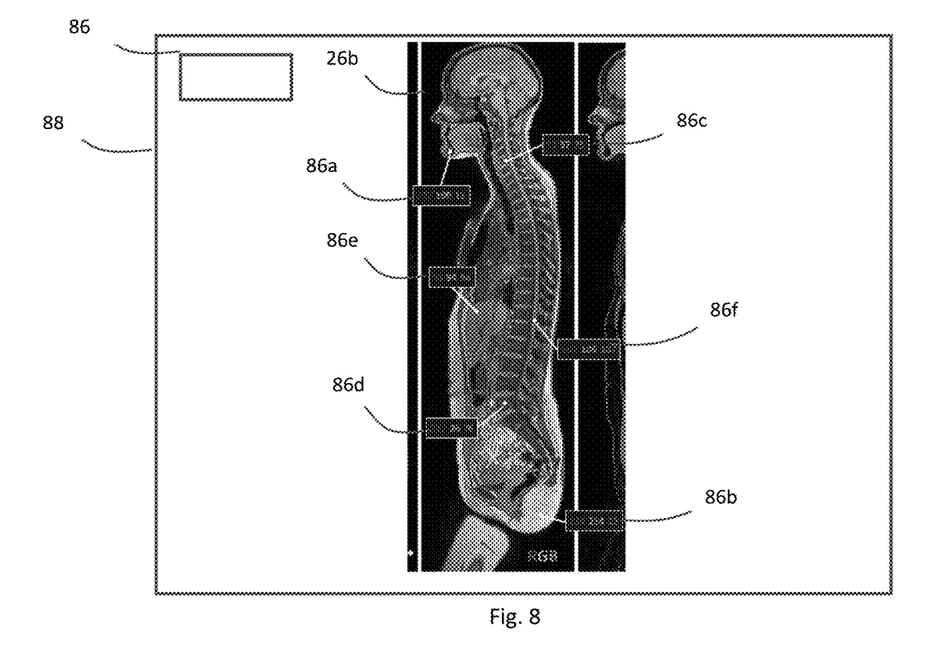
FIG. 8 illustrates a graphical user interface displaying a color encoded composite image according to one embodiment of the invention.

The RGB composite image 26b of FIGS. 2A and 8 shows six different RGB values (86a-86f) for six different voxels of composite image 26b and illustrates how the RGB encoding produces yellow, magenta, and the appearance of grayscale. For instance, voxels that are primarily fat (e.g., values 86a and 86b), have high IP (R) and OP (G) values and low W (B) values. Since red (R) plus green (G) yields yellow (Y), these voxels have a yellowish hue. Voxels representing vertebral hematopoietic marrow (values 86c and 86d) have high IP (R), moderate W (B), and somewhat lower OP (G). Voxels for the liver and spinal cord (values 86e and 86f) have nearly the same values for IP, OP, and W, which produces the appearance of grayscale. The values for IP, OP, and W approach parity (i.e., approach grayscale) as the fat content and T2* decay approaches zero. As those skilled in the art will appreciate, exact parity between IP, OP, and W is not necessary to achieve the appearance of grayscale. The differences between IP and OP for values 86e and 86f are not discernable in the composite image.

For FIGS. 3-7, we color-encoded 3D fast Dixon cases obtained from teaching files that contained OP, IP, W, and F images. All available images had been obtained on Siemens scanners. Exams performed at 1.5 T had dual TEs of 2.4 and 4.6 ms; and at 3.0 T had dual TEs of 1.2-1.4 and 2.4-2.6 ms. Abdominal studies reviewed were acquired in the axial plane and predominately at 1.5 T (FIGS. 3-5 and 7), while studies covering the head, neck, and spine were performed at 3 T and primarily acquired in the sagittal plane with subsequent multiplanar reformations. (FIG. 6) Where available studies were compared to multi-echo PDFF quantification of fat and iron content.

Figure 3:
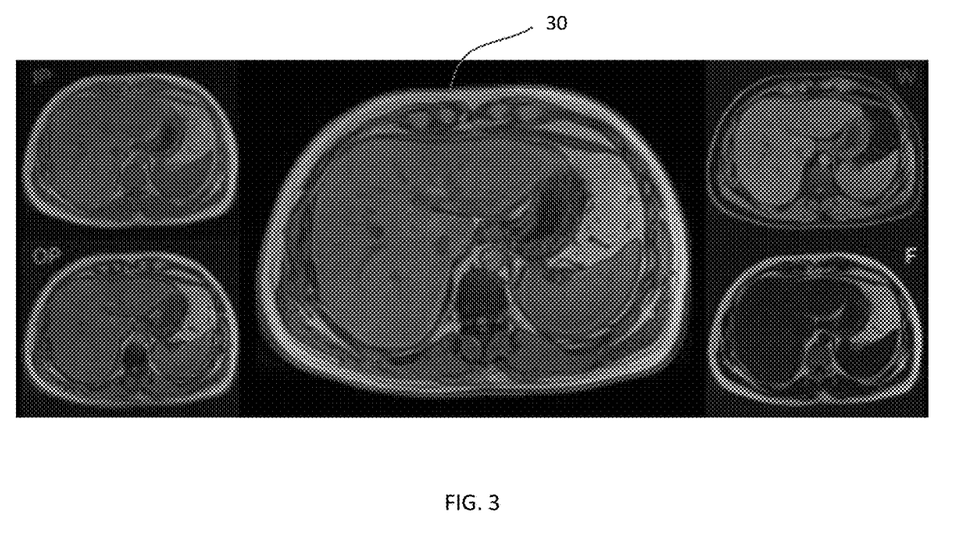
FIG. 3 shows color encoded composite images of a patient with hepatic steatosis without iron deposition.

FIG. 3 shows a color encoded composite image 30 of a patient with hepatic steatosis without iron deposition. Image maps W, OP, and IP were used to generate composite image 30.

Figure 4:
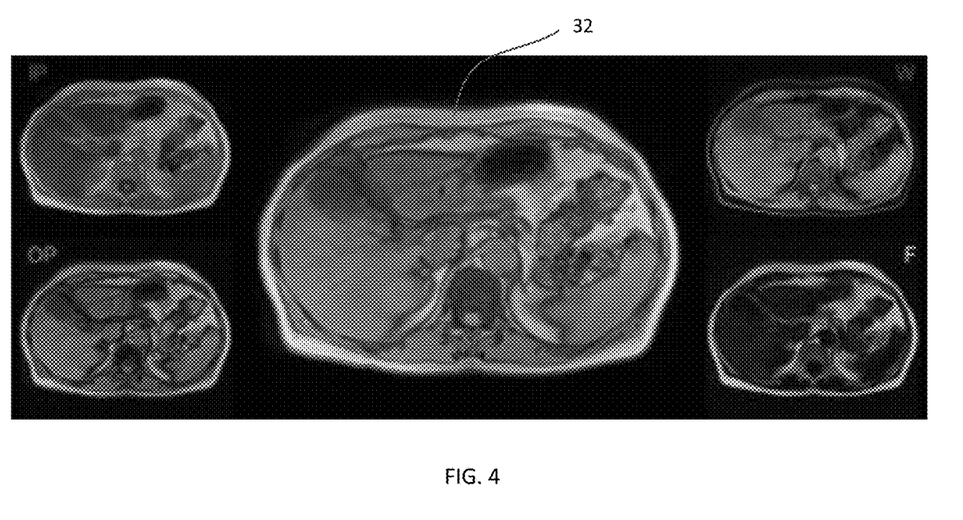
FIG. 4 shows RGB color-encoded Dixon image of a patient with iron accumulation in the liver.

FIG. 4 shows an RGB color-encoded Dixon image 32 of a patient with iron accumulation in the liver. Image maps W, OP, and IP were used to generate composite image 32.

Figure 5:
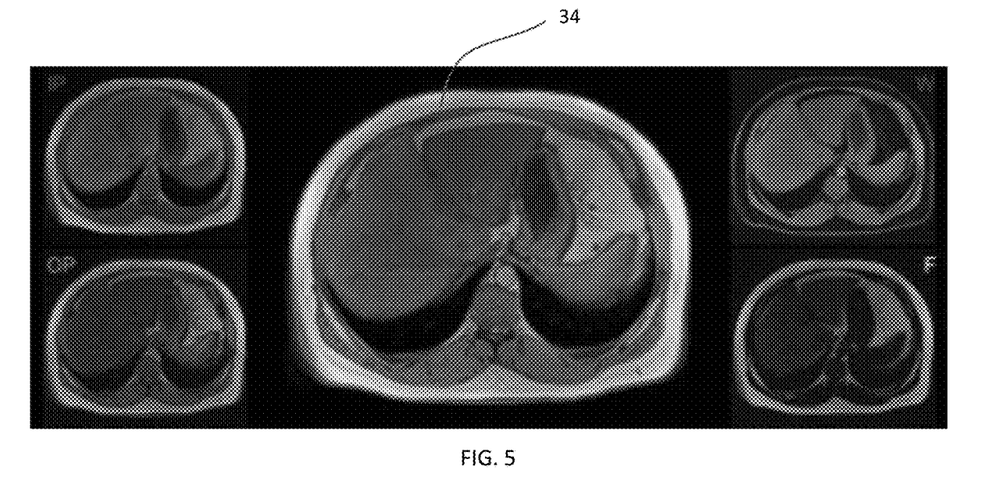
FIG. 5 shows RGB color-encoded Dixon images of a patient found to have diffuse hepatic steatosis and no evidence of iron overload.

FIG. 5 shows an RGB color-encoded Dixon image 34 of a patient found to have diffuse hepatic steatosis and no evidence of iron overload. Image maps W, OP, and IP were used to generate composite image 34.

Figure 6:
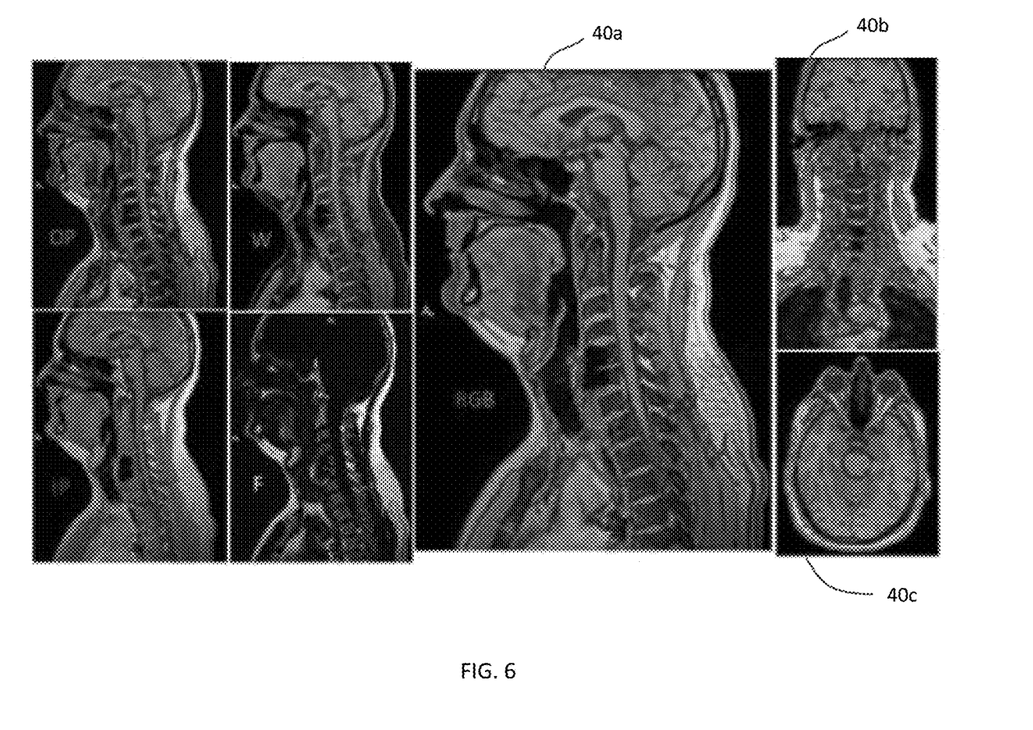
FIG. 6 shows RGB color-encoded Dixon images of a patient with a metallic implant yielding local magnetic susceptibility artifact.

FIG. 6 shows RGB color-encoded Dixon images (40a-40c) of a patient with a metallic implant yielding local magnetic susceptibility artifact. Image maps W, OP, and IP were used to generate composite images 40a-40c.

Figure 7:
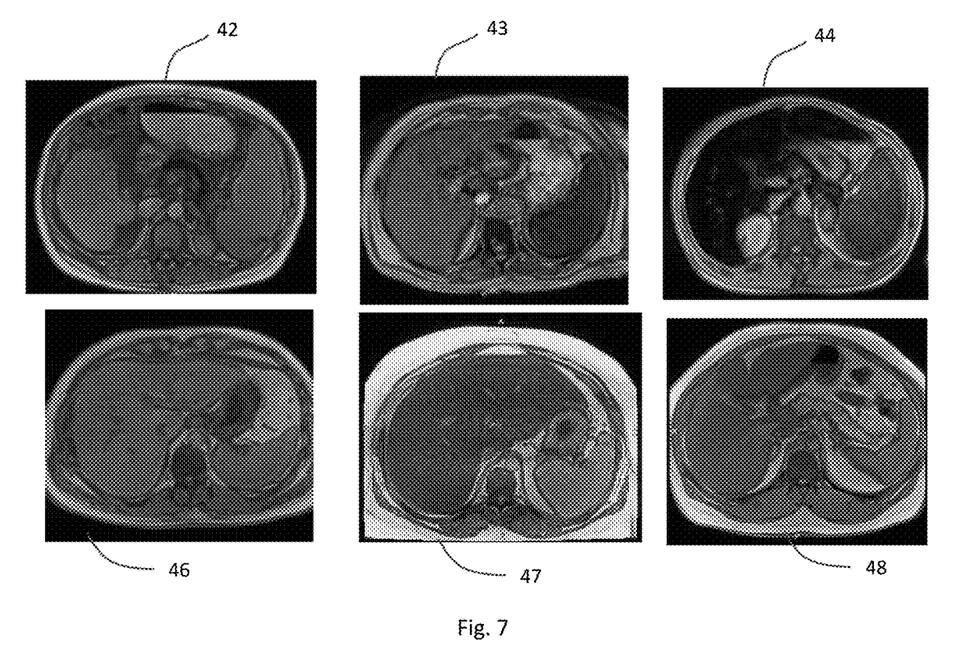
FIG. 7 shows RGB color-encoded Dixon images of patients with varying degrees of iron overload (top row) or steatosis (bottom row)

FIG. 7 shows RGB color-encoded Dixon images of patients with varying degrees of iron overload (42-44) or steatosis (46-48).

The color-encoding in FIGS. 3-7 use additive color mixing to represent tissue properties. Tissues containing water have similar IP, OP and W intensity and mix to shades of gray. Using the default color encoding scheme, tissues containing macroscopic fat lack W signal intensity and appear yellow. With contrast administration, however, fat shifts slightly in hue and saturation toward orange as OP signal (G) decreases in conjunction with the relative increase in W signal (B).

Tissues containing both fat and water have a red-to-magenta hue as do regions with "India ink" artifact (which appears black on OP images) since IP intensity (R) predominates and OP intensity (G) is diminished or nulled. (FIG. 3) Regions of magnetic susceptibility or tissues demonstrating significant T2* decay appear greenish due to signal decay between the first OP (G) and second IP (R) echo. (FIG. 4) Consequently, iron deposition in the liver and other organs appears green (FIG. 4, top row FIG. 7) as do regions of susceptibility artifact (FIG. 6) while steatosis appears red (FIGS. 3,4, bottom row FIG. 7).

If a 3-point Dixon or longer multi-echo CSE sequence is utilized, the effects of F/W dephasing and T2* relaxation can be separated, alleviating the ambiguity arising from 2-point Dixon analysis of tissues with steatosis plus iron overload. A color encoded composite of hepatic dual pathology wherein RGB values reflect the first two IP & OP echoes and T2* corrected W values, should not appear gray (R=G=B) as the T2* corrected W value would exceed the OP value, the latter being reduced by both F/W dephasing and T2* relaxation.

None of the fast Dixon cases reviewed demonstrated a total fat-water swap. One case with sagittal volumetric sequencing at 1.4 mm thickness demonstrated a very small focal area of mis-mapping anterior to metallic ACD&F hardware that was not seen when acquired with 1 mm thickness. (FIG. 6). At 3 T, short echo times, high BW, small voxels size, and short acquisition times mitigate artifact related to motion, pulsation, and magnetic susceptibility.

Both RGB and L*a*b* color composites behaved similarly, were intuitive (e.g. yellow marrow—Y, red marrow—R), and facilitated interpretation.

Some embodiments of the computer apparatus include a graphical user interface (GUI) that is configured to display the color composite images and receive input to interrogate individual voxels or groups of voxels in the color composite images. FIG. 8 illustrates a GUI 88, including a selectable menu 7, and configured to display the color composite image 26b of FIG. 2A on a display screen and receive input from a user for selecting one or more of the display voxels (e.g., through a pointer selection made using a mouse).

The GUI 88 response to the selection (i.e., interrogation of the voxel) is to display on the GUI 88 the values related to the voxel and/or its color encoding. Upon user interrogation of the voxel(s), the computing apparatus may provide one or more of the following or combinations of the following: (i) RGB values, (ii) the input values from which the RGB values are derived, (iii) intensity values of the chemical shift encoded MRI's echo train, (iv) a plot of the echo train values, (v) derivable values from the chemical shift encoded MRI, and/or (vi) intensity or derivable values from another MRI series that can be co-registered to the color composite being interrogated.

The combination of color encoding with the ability to interrogate voxel values allows the user/clinician to quickly identify voxels of interest (i.e., based on color and anatomy) and then look up voxel values. The user can quickly explore a region of voxels or across an anatomical boundary to better understand the variation in the values in a region or along a boundary.

RGB composites typically afford direct decomposition/interrogation of underlying IP, OP, & W intensities with standard GUIs as they respectively correspond to R, G, and B pixel values; while in the case of CIE L*a*b* color composites, look up tables may be required.

As the 2-point Dixon color encoding technique is inherently qualitative rather than quantitative; for hepatic evaluation, if the liver appears green suggesting iron overload or red suggesting steatosis, quantitative confounder-corrected chemical shift encoded MRI (CSE-MRI) should be considered for further evaluation. Such quantitative CSE MRI may also be warranted if the liver appears gray but dual pathology (steatosis plus iron overload) is suggested by Boll analysis or by comparing the W intensity of liver voxels to those of other gray appearing soft tissues such as the conus which would not be expected to manifest steatosis plus iron overload. Additional details regarding the Boll technique can be found in DT, Marin D, Redmon G M, Zink S I, Merkle E M, "Pilot Study Assessing Differentiation of Steatosis Hepatis, Hepatic Iron Overload, and Combined Disease Using Two-Point Dixon MRI at 3 T: In Vitro and In Vivo Results of a 2D Decomposition Technique," American Journal of Roentgenology, 2010 Apr. 1; 194(4):964-71, which is hereby incorporated by reference.

The overall goal was to develop a simple, intuitive and clinically useful color presentation that integrates multiple contrasts obtained in Dixon acquisitions. By facilitating the interpretation of complex Dixon data sets we can increase utilization of Dixon across the entire body.

Figure 9:
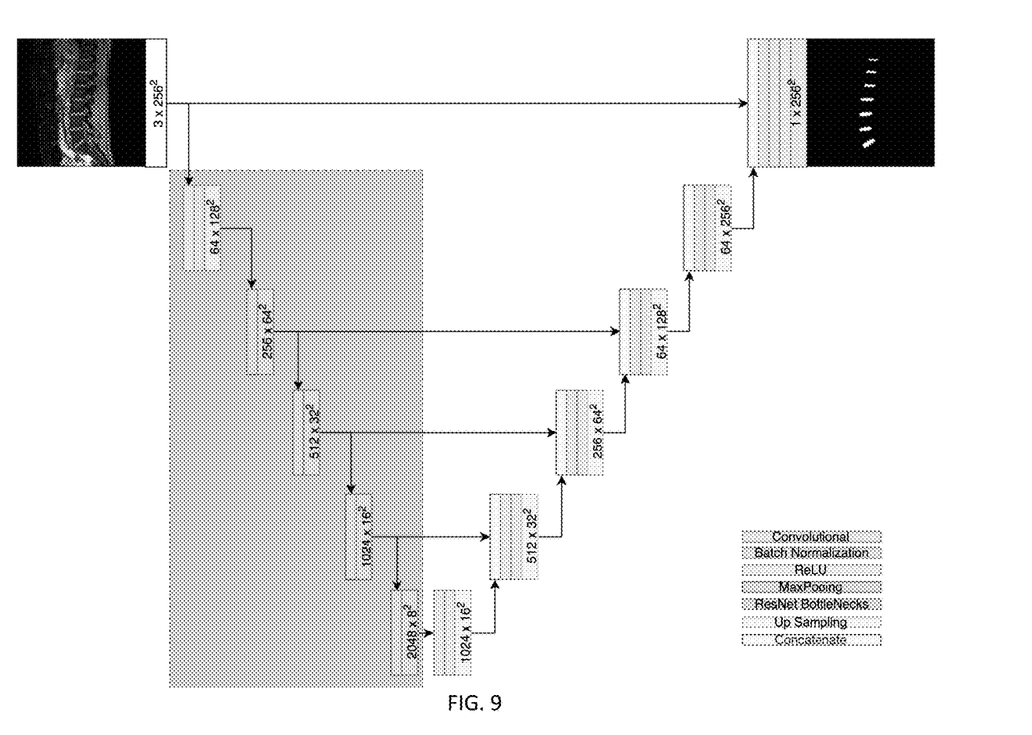
FIG. 9 illustrates an architecture for a convolution neural network to extract features from RGB color-encoded Dixon images and generate an output.
Figure 10:
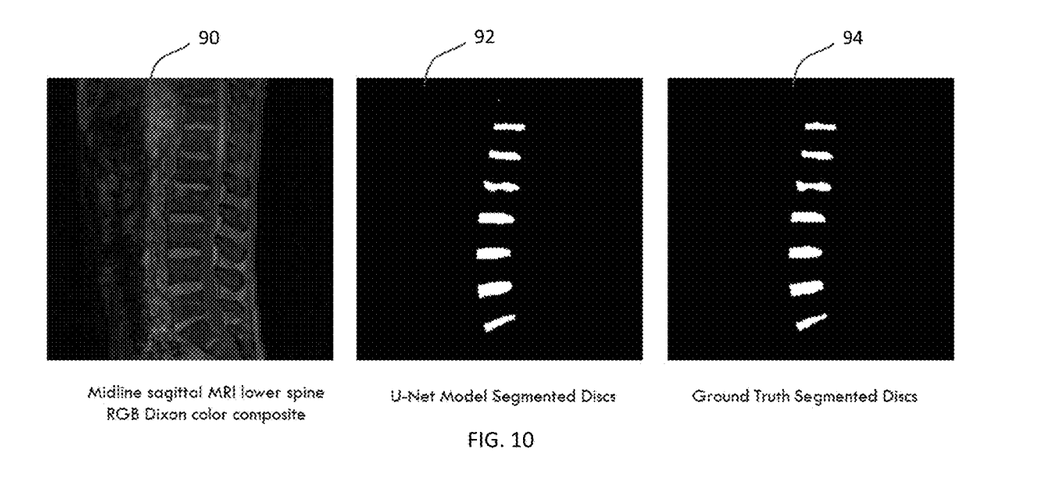
FIG. 10 shows a sample result from the U-Net Model illustrated in FIG. 9.

Additionally, the color RGB representation of Dixon images may facilitate artificial intelligence computer vision applications that rely on transfer learning of pre-trained color vision neural networks. FIG. 9 illustrates how a convolution neural network, such as ResNet-50 can extract features from RGB color-encoded Dixon images to computer generate a desired output; in this case, segmented intervertebral discs. FIG. 10 shows a sample result from the U-Net Model illustrated in FIG. 9. The intervertebral discs which appear gray on RGB color-encoded Dixon spine image 90 are well segmented and shown in white in image 92 and closely approximating the ground truth segmented discs in image 94.

For FIG. 10, ResNet-50, a convolution neural network, was used to extract features from RGB color-encoded images derived from the 2018 IVDM3Seg Challenge Dixon data sets. Transfer learning was implemented by using weights pretrained on ImageNet utilizing large RGB datasets to initialize the ResNet-50 backbone. The backbone model was fixed and the model was trained for 10 epochs. Subsequently, the backbone was unfrozen and the whole model trained for 50 epochs. Despite the limited number of Challenge Dixon data sets provided, good intervertebral disc segmentation was achieved with average Intersection over Union (IoU) of 0.815. This was improved to 0.816 by data augmentation utilizing synthetic data generated by changing contrast and adding Gaussian noise; and to 0.824 by combining with results obtained from coronal reformats of the provided sagittal data sets similarly trained on ResNet-50. (FIG. 10)

Dixon and other multi-echo CSE sequences can generate robust fat maps. As such, these sequences or fat maps derived therefrom can be used to help identify and if desired enhance or suppress fat signal in other co-registered imaging studies of the same patient. While this can be accomplished by direct mapping of one study on the other, image misregistration may well yield significant artifacts. Consequently, convolution neural networks hold promise to improve results. Using information from multi-echo CSE sequences or derived maps, CNNs may also be able to improve the image quality of co-registered images. This may be done post hoc or during image reconstruction.

In one embodiment a computer apparatus that identifies fat containing voxels in a patient's imaging study includes:
  a) a non-transitory memory storing the imaging study plus a multi-echo CSE MRI sequence or fat maps derived therefrom covering the patient's same anatomy;
  b) a program stored in the non-transitory memory and operatively configured to co-register these studies and directly or via convolutional neural network identify fat voxels in said imaging study;
  c) a computer processor in communication with the non-transitory memory and configured to perform the program by executing computer executable instructions.

Alternatively, or in addition, identified fat containing voxels in said imaging study are:
  a) color or otherwise encoded to reflect lipid content, b) enhanced,
c) suppressed or
d) used in part to improve image quality Additional details regarding MRI techniques that can be used in combination with the features of the present invention are described in the following references, which are hereby incorporated by reference.

References

1. Dixon, W. T. (1984). Simple proton spectroscopic imaging. Radiology 153, 189-194.
2. Bray T J P, Singh S, Latifoltojar A, Rajesparan K, Rahman F, Narayanan P, et al.
   Diagnostic utility of whole-body Dixon MRI in multiple myeloma: A multi-reader study. PLoS ONE. 2017; 12(7): e0180562.
3. Kather J N, Weidner A, Attenberger U, Bukschat Y, Weis C-A, Weis M, et al. Color-coded visualization of magnetic resonance imaging multiparametric maps. Sci Rep. 2017 23; 7:41107.
4. Weiss K L, Stiving S O, Herderick C E, Cornhill J F, Chakeres D W. Hybrid Color M R Imaging Display. AJR Oct 1987; 149:825-829
5. Weiss K L, Welsh R C, Dong Q, Weadock W J, Shah G V. Multiparametric Color-encoded Brain MR Imaging in Talairach Space. RadioGraphics. 2002 March-April; 22(2):E3-3
6. Weiss K L, Richards C R, Sun D, Weiss J L. Subminute Fat-Water-Separated Dual-Echo Automated Spine Survey Iterative Scan Technique. American Journal of Neuroradiology. 2009 Nov. 1; 30(10):1840-6.
7. Boll D T, Marin D, Redmon G M, Zink S I, Merkle E M. Pilot Study Assessing Differentiation of Steatosis Hepatis, Hepatic Iron Overload, and Combined Disease Using Two-Point Dixon MRI at 3 T: In Vitro and In Vivo Results of a 2D Decomposition Technique. American Journal of Roentgenology. 2010 Apr. 1; 194(4):964-71.
8. Reeder, S. B., Cruite, I., Hamilton, G., and Sirlin, C. B. (2011). Quantitative assessment of liver fat with magnetic resonance imaging and spectroscopy. J Magn Reson Imaging 34, 729-749.
9. Hong, C. W., Fazeli Dehkordy, S., Hooker, J. C., Hamilton, G., and Sirlin, C. B. (2017). Fat Quantification in the Abdomen. Topics in Magnetic Resonance Imaging 26, 221.
10. Weiss K L, Storrs J M, Roda M S. Fast Multiparametric 3D Spine MRI: Color Me Dixon! Miami, Fla.: ASSR 2019: February 20-24.
11. Weiss K L, Storrs J M, Roda M S. Color-Encoded Multiparametric 3D Fast Dixon. Montreal, Canada: ISMRM 2019: May 11-17.

Computer Program Products

Figure 11:
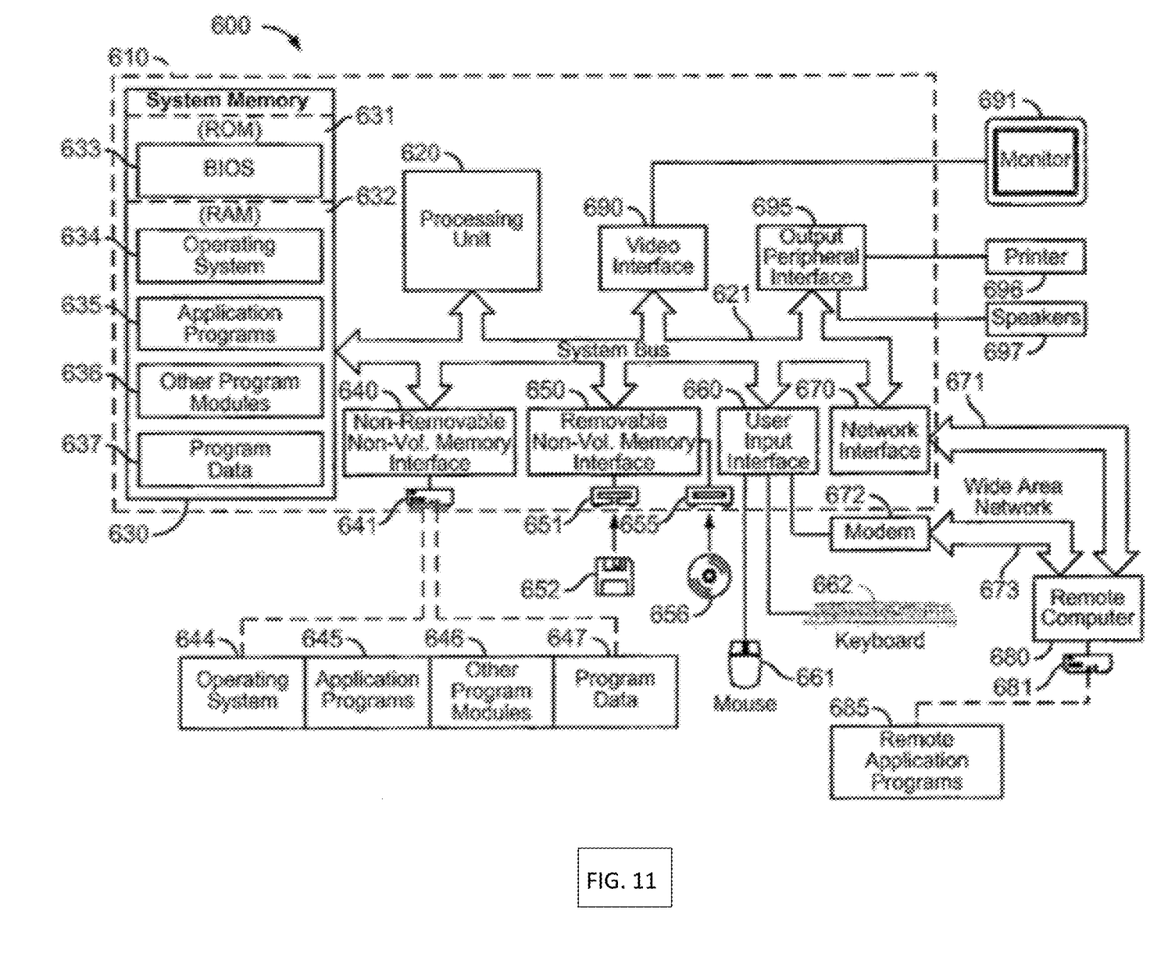
FIG. 11 illustrates a computer apparatus in which the color encoding of the present invention can be carried out.

An example of a computing environment for implementing the present technology is shown in FIG. 11. For example, the computing environment shown in FIG. 11 can be an example of the means for performing the acts and steps disclosed herein including those means incorporated herein. Therefore, the acts and steps of the claims can be performed by a specially programmed computer or a computer readable medium, such as optical or magnetic media with computer executable instructions stored thereon. FIG. 11 illustrates a computing environment 600 for implementing the present technology. In one embodiment, the computing environment 600 may implement the servers of systems disclosed herein as well as client devices disclosed herein.

Computing environment 600 is only one example of a suitable computing environment and is not intended to suggest any limitation as to the scope of use or functionality of the technology herein. Neither should the computing environment 600 be interpreted as having any dependency or requirement relating to any one or combination of components illustrated in the exemplary operating environment 600.

The technology described herein is operational with numerous other general-purpose or special purpose computing system environments or configurations. Examples of well-known computing systems, environments, and/or configurations that may be suitable for use with the technology herein include, but are not limited to, personal computers, server computers, hand-held or laptop devices, mobile phones or devices, multiprocessor systems, microprocessor-based systems, set top boxes, programmable consumer electronics, network PCs, minicomputers, mainframe computers, distributed computing environments that include any of the above systems or devices, and the like.

The technology herein may be described in the general context of computer-executable instructions, such as program modules, being executed by a computer. Generally, program modules include routines, programs, objects, components, data structures, etc., that perform particular tasks or implement particular abstract data types. The technology herein may also be practiced in distributed computing environments where tasks are performed by remote processing devices that are linked through a communications network. In a distributed computing environment, program modules may be located in both local and remote computer storage media including memory storage devices.

With reference to FIG. 10, an exemplary system for implementing the technology herein includes a general-purpose computing device in the form of a computer 610. Components of computer 610 may include, but are not limited to, a processing unit 620, a system memory 630, and a system bus 621 that couples various system components including the system memory to the processing unit 620. The system bus 621 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

Computer 610 typically includes a variety of computer readable media. Computer readable media can be any available media that can be accessed by computer 610 and includes both volatile and nonvolatile media, removable and non-removable media. By way of example, and not limitation, computer readable media may comprise computer storage media and communication media. Computer storage media includes both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can accessed by computer 610. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media.

The system memory 630 includes computer storage media in the form of volatile and/or nonvolatile memory such as read only memory (ROM) 631 and random access memory (RAM) 632. A basic input/output system 633 (BIOS), containing the basic routines that help to transfer information between elements within computer 610, such as during start-up, is typically stored in ROM 631. RAM 632 typically contains data and/or program modules that are immediately accessible to and/or presently being operated on by processing unit 620. By way of example, and not limitation, FIG. 11 illustrates operating system 634, application programs 635, other program modules 636, and program data 637.

The computer 610 may also include other removable/non-removable, volatile/nonvolatile computer storage media. By way of example only, FIG. 11 illustrates a hard disk drive 640 that reads from or writes to non-removable, nonvolatile magnetic media, a magnetic disk drive 651 that reads from or writes to a removable, nonvolatile magnetic disk 652, and an optical disk drive 655 that reads from or writes to a removable, nonvolatile optical disk 656 such as a CD ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 641 is typically connected to the system bus 621 through an non-removable memory interface such as interface 640, and magnetic disk drive 651 and optical disk drive 655 are typically connected to the system bus 621 by a removable memory interface, such as interface 650.

The drives and their associated computer storage media discussed above and illustrated in FIG. 11, provide storage of computer readable instructions, data structures, program modules and other data for the computer 610. In FIG. 11, for example, hard disk drive 641 is illustrated as storing operating system 644, application programs 645, other program modules 646, and program data 647. Note that these components can either be the same as or different from operating system 634, application programs 635, other program modules 636, and program data 637. Operating system 644, application programs 645, other program modules 646, and program data 647 are given different numbers here to illustrate that, at a minimum, they are different copies. A user may enter commands and information into the computer 60 through input devices such as a keyboard 662 and pointing device 661, commonly referred to as a mouse, trackball or touch pad. Other input devices (not shown) may include a microphone, joystick, game pad, satellite dish, scanner, or the like. These and other input devices are often connected to the processing unit 620 through a user input interface 660 that is coupled to the system bus, but may be connected by other interface and bus structures, such as a parallel port, game port or a universal serial bus (USB). A monitor 691 or other type of display device is also connected to the system bus 621 via an interface, such as a video interface 690. In addition to the monitor, computers may also include other peripheral output devices such as speakers 697 and printer 696, which may be connected through a output peripheral interface 690.

The computer 610 may operate in a networked environment using logical connections to one or more remote computers, such as a remote computer 680. The remote computer 680 may be a personal computer, a server, a router, a network PC, a peer device or other common network node, and typically includes many or all of the elements described above relative to the computer 610, although only a memory storage device 681 has been illustrated in FIG. 11. The logical connections depicted in FIG. 11 include a local area network (LAN) 671 and a wide area network (WAN) 673, but may also include other networks. Such networking environments are commonplace in offices, enterprise-wide computer networks, intranets and the Internet.

When used in a LAN networking environment, the computer 610 is connected to the LAN 671 through a network interface or adapter 670. When used in a WAN networking environment, the computer 610 typically includes a modem 672 or other means for establishing communications over the WAN 673, such as the Internet. The modem 672, which may be internal or external, may be connected to the system bus 621 via the user input interface 660, or other appropriate mechanism. In a networked environment, program modules depicted relative to the computer 610, or portions thereof, may be stored in the remote memory storage device. By way of example, and not limitation, FIG. 11 illustrates remote application programs 685 as residing on memory device 681. It will be appreciated that the network connections shown are exemplary and other means of establishing a communications link between the computers may be used.

The present invention may be embodied in other specific forms without departing from its spirit or characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A computer apparatus and color encoding scheme to facilitate the interpretation and analysis of a multi-echo chemical shift encoded (CSE) MRI of a vertebrate organism, comprising:
   (a) a non-transitory memory storing images generated from a gradient echo (GRE containing) multi-echo CSE MRI sequence;
   (b) a program stored in the non-transitory memory and operatively configured to generate a three-dimensional color space composite output image utilizing at least three stored images as inputs, wherein:
      (i) the at least three input images are inherently co-registered and have at least three different image types selected from the group consisting of in-phase (IP), opposed-phase (OP), water (W), fat (F), R2* (1/T2*), and derivatives of these;
      (ii) output image voxels whose MRI signal derives at least in part from water protons approach grayscale as the contribution of lipid protons and T2* signal decay approach zero;
      (iii) output image voxels exhibit a color that deviates from gray based in part on lipid proton content and T2* signal decay; and (iv) at least a portion of the output image voxels exhibit a color that includes and provides information from corresponding voxels in each of the input images; and (c) a computer processor in communication with the non-transitory memory and configured to perform the program by executing computer executable instructions.

2. The apparatus of claim 1, wherein the at least three images include Dixon in phase (IP), opposed phase (OP), and derived water (W) images.

3. The apparatus of claim 1, wherein at least a portion of the stored images are obtained using the iterative decomposition of water with echo asymmetry and least-squares estimation (IDEAL) technique.

4. The apparatus of claim 1 wherein the color composite image is encoded in the RGB color space.

5. The apparatus of claim 4, wherein the at least three image maps include OP, IP, and W series, each of which is assigned a different color channel selected from R, G, and B in the RGB color space.

6. The apparatus and method of claim 5 wherein the OP, IP, and W series are respectively assigned to the R, G, and B channels.

7. The apparatus of claim 2, wherein the color space is CIE L*a*b*.

8. The apparatus of claim 1, wherein the color space is CIE L*a*b* and wherein:

L=IP+OP, a=(IP−OP)/(IP+OP), and b=(IP+OP−2W)/(IP+OP); or L=x*(IP+OP), a=y*(IP−OP), b=z*(IP+OP−2W).

9. The apparatus of claim 8 wherein x=50, y=100, and z=50.

10. The apparatus of claim 1 wherein soft tissue voxels containing both iron and fat are identified and specially encoded to enhance their conspicuity.

11. The apparatus of claim 10 wherein the soft tissue voxels are identified by the Boll technique, by comparing to reference soft tissue voxels that are not expected to contain iron or fat, or by comparison to a co-registered longer echo train CSE MRI that demonstrates the presence of both steatosis and iron overload.

12. The apparatus of claim 10 wherein the voxels are uniquely color encoded.

13. The apparatus of claim 1, wherein the color space composites generated are used as an input in an artificial intelligence application.

14. The apparatus of claim 13, wherein the artificial intelligence application involves computer vision and relies on transfer learning of convolutional neural networks pre-trained with color images.

15. The apparatus of claim 1, wherein the acquired images are selected from the group consisting of gradient echo images, spin echo images, and combinations thereof.

16. The apparatus of claim 1, wherein the derived images are selected from the group consisting of PDFF (proton density fat fraction), PDWF (proton density water fraction), R2*, T2*, W (water), F (fat), W %, or F %.

17. The apparatus of claim 1, wherein the multi-echo chemical shift encoded (CSE) MRI sequence is a dual echo (two point) Dixon sequence.

18. The apparatus of claim 17, wherein the dual echoes are gradient echoes, the first being opposed phase and the second being in phase.

19. The computer apparatus of claim 1, further comprising:

a graphical user interface configured to display the color composite image on a display screen and receive input from a user for selecting one or more voxels being displayed, wherein in response to the selection, one or more values of the selected one or more voxels are displayed on the graphical user interface.

20. The computer apparatus of claim 19, wherein the one or more values are selected from one or more of the following or combinations thereof:

(i) RGB values;
(ii) an input value from which the RGB values are derived,
(iii) intensity values of a chemical shift encoded MRI's echo train;
(iv) a plot of the echo train values;
(v) derivable values from a chemical shift encoded MRI; or
(vi) intensity or derivable values from another MRI series that is co-registered to the color composite being interrogated.

* * * * *